(12) United States Patent
Fonger et al.

(10) Patent No.: US 8,771,173 B2
(45) Date of Patent: Jul. 8, 2014

(54) ACCESS DEVICE FOR SURGERY

(75) Inventors: James Fonger, Atlanta, GA (US); Chris Jorgensen, Bethesda, MD (US); Kevin Rego, Marietta, GA (US); Tahir Haque, Atlanta, GA (US); Nick Patel, North East, MD (US)

(73) Assignee: Saint Joseph's Translational Research Institute, Inc., Atlanta, GA (US)

( * ) Notice: Subject to any disclaimer, the term of this patent is extended or adjusted under 35 U.S.C. 154(b) by 262 days.

(21) Appl. No.: 13/090,088

(22) Filed: Apr. 19, 2011

(65) Prior Publication Data

US 2012/0149982 A1 Jun. 14, 2012

Related U.S. Application Data

(60) Provisional application No. 61/422,931, filed on Dec. 14, 2010.

(51) Int. Cl.
*A61B 1/00* (2006.01)

(52) U.S. Cl.
USPC ........... 600/114; 600/106; 600/107; 600/127; 600/129; 600/208

(58) Field of Classification Search
USPC .................. 600/106–107, 114–115, 127, 129
See application file for complete search history.

(56) References Cited

U.S. PATENT DOCUMENTS

| | | | | |
|---|---|---|---|---|
| 3,850,175 A | * | 11/1974 | Iglesias | 606/46 |
| 4,132,227 A | * | 1/1979 | Ibe | 600/105 |
| 4,825,259 A | * | 4/1989 | Berry, Jr. | 356/241.4 |
| 5,047,848 A | * | 9/1991 | Krauter | 348/82 |
| 5,448,990 A | * | 9/1995 | De Faria-Correa | 600/129 |
| 5,681,262 A | * | 10/1997 | Isse | 600/127 |
| 5,716,321 A | * | 2/1998 | Kerin et al. | 600/114 |
| 5,725,479 A | * | 3/1998 | Knight et al. | 600/210 |
| 5,827,216 A | | 10/1998 | Igo et al. | |
| 6,042,538 A | * | 3/2000 | Puskas | 600/114 |
| 6,193,653 B1 | * | 2/2001 | Evans et al. | 600/210 |

(Continued)

FOREIGN PATENT DOCUMENTS

WO 2009149421 12/2009

OTHER PUBLICATIONS

International Search Report issued Jun. 19, 2012 in PCT/US2011/064782.

(Continued)

*Primary Examiner* — Matthew J Kasztejna
(74) *Attorney, Agent, or Firm* — Meunier Carlin & Curfman LLC

(57) ABSTRACT

The present invention provides an access device for surgery. The access device includes a guide member and a head member. The guide member and head member define a channel configured to receive and guide a sterile flexible scope with a working channel. The guide member and head member cooperate to extend through a small opening of 2 cm or less to access tissue structures. The head member may include surfaces to separate a pericardium from a surface of the heart, stabilize a beating heart and, with the endoscope, provide visibility for the implantation of a therapeutic such as stem cells to the surface of the heart with improved safety and accuracy. Ranges of other diagnostic, application of therapeutics or biologics, and observational applications may be facilitated by the access device, such as TMR, ablation, echo-probe diagnostics, LAA isolation, observation of the same procedures, etc.

15 Claims, 9 Drawing Sheets

(56) References Cited

U.S. PATENT DOCUMENTS

| | | | |
|---|---|---|---|
| 6,206,823 B1* | 3/2001 | Kolata et al. | 600/129 |
| 6,675,042 B2 | 1/2004 | Swerdlow et al. | |
| 6,805,860 B1 | 10/2004 | Alt | |
| 6,837,848 B2* | 1/2005 | Bonner et al. | 600/114 |
| 6,908,427 B2* | 6/2005 | Fleener et al. | 600/104 |
| 7,257,441 B2 | 8/2007 | Swerdlow et al. | |
| 7,341,554 B2* | 3/2008 | Sekine et al. | 600/106 |
| 7,398,781 B1* | 7/2008 | Chin | 128/898 |
| 7,854,109 B2 | 12/2010 | Zubiate et al. | |
| 7,871,408 B2 | 1/2011 | Krishnan et al. | |
| 8,075,478 B2* | 12/2011 | Campos | 600/139 |
| 8,328,808 B2* | 12/2012 | Guzman et al. | 606/68 |
| 8,376,932 B2* | 2/2013 | Hashiba et al. | 600/104 |
| 2003/0009085 A1* | 1/2003 | Arai et al. | 600/127 |
| 2003/0195569 A1 | 10/2003 | Swerdlow et al. | |
| 2004/0087831 A1 | 5/2004 | Michels et al. | |
| 2004/0106955 A1 | 6/2004 | Swerdlow et al. | |
| 2005/0261673 A1 | 11/2005 | Bonner et al. | |
| 2006/0200118 A1 | 9/2006 | Krishnan et al. | |
| 2006/0258906 A1 | 11/2006 | Binmoeller | |
| 2007/0123748 A1 | 5/2007 | Meglan et al. | |
| 2007/0255109 A1 | 11/2007 | Stein et al. | |
| 2008/0051841 A1 | 2/2008 | Swerdlow et al. | |
| 2008/0135709 A1 | 6/2008 | Zubiate et al. | |
| 2008/0230054 A1 | 9/2008 | Prineas | |
| 2009/0326511 A1 | 12/2009 | Shivkumar | |
| 2010/0010442 A1 | 1/2010 | Shivkumar et al. | |

OTHER PUBLICATIONS

Fujimura et al. "Direct in vivo visualization of right cardiac anatomy by fibreoptic endoscopy: observation of radiofrequency-induced acute lesions around the ostium of the coronary sinus," Eur Heart J. Apr. 1994; 15(4):534-540.

Takeyoshi et al. "Percutaneous Subxiphoid Access to the Epicardium Using a Miniature Crawling Robotic Device," Innovations. 2006;1(5):5.

UCLA Health System. UCLA Cardiac Arrhythmia Center. Los Angeles, CA, Printed on Apr. 14, 2011 http://arrhythmia.ucla.edu/body.cfm?id=20#stereotaxis.

Yun-sheng et al. "AKT-modified autologous intracoronary mesenchymal stem cells prevent remodeling and repair in swine infracted myocardium," Chinese Medical Journal 2010; 123(13): 1702-1708.

Zenati et al. "Left Heart Pacing Lead Implantation Using Subxiphoid Videopericardioscopy," Journal of Cardiovascular Electrophysiology 2003; 14(9):949-953.

* cited by examiner

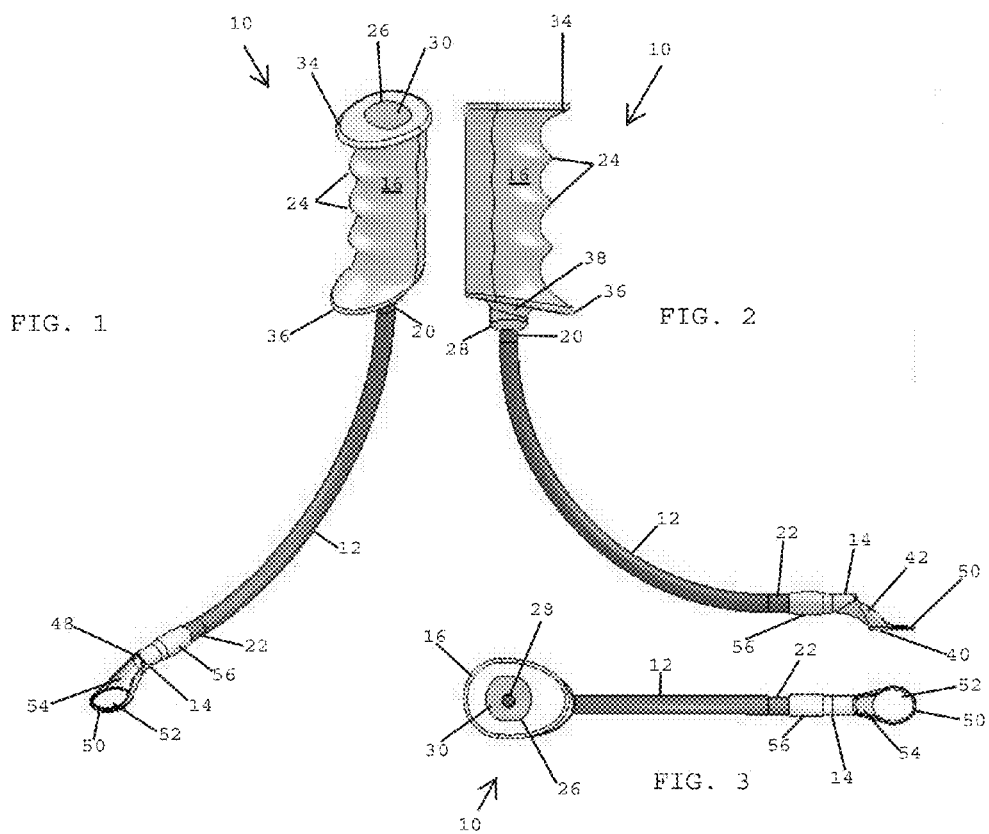

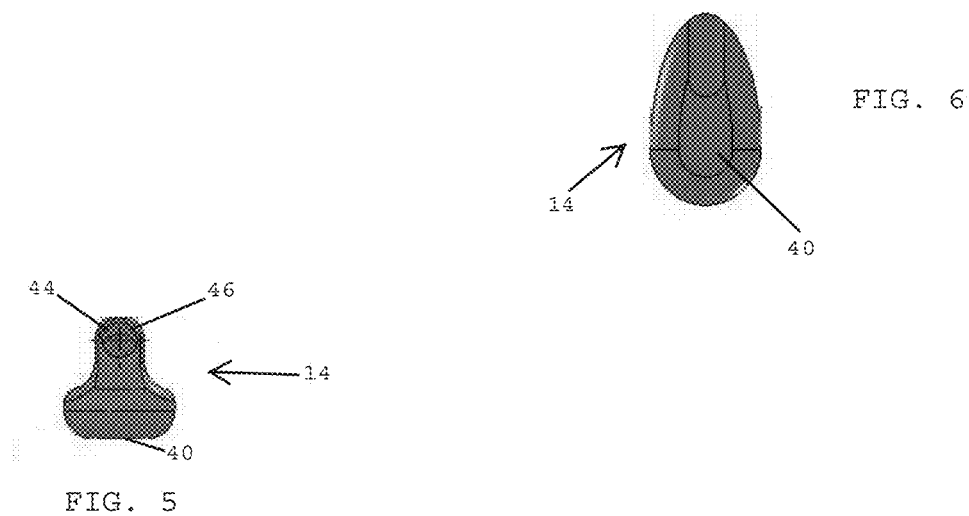
FIG. 6
FIG. 5
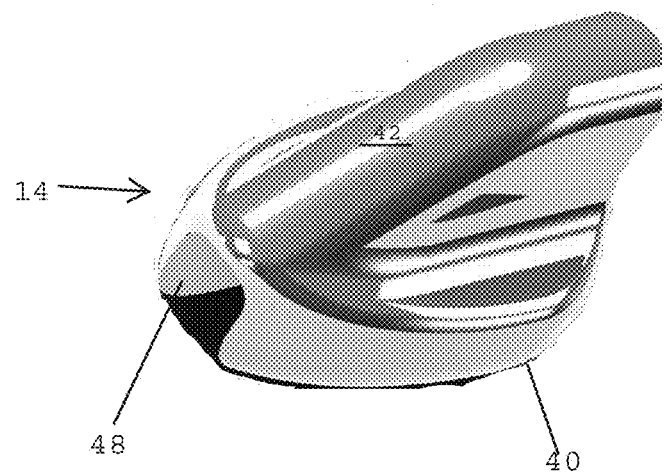
FIG. 4

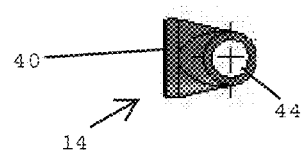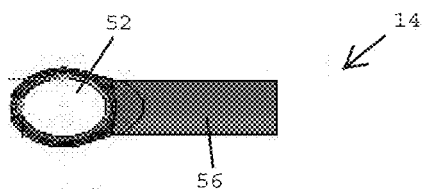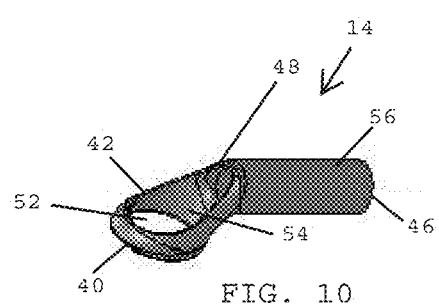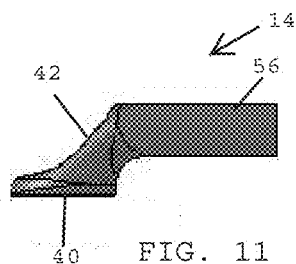

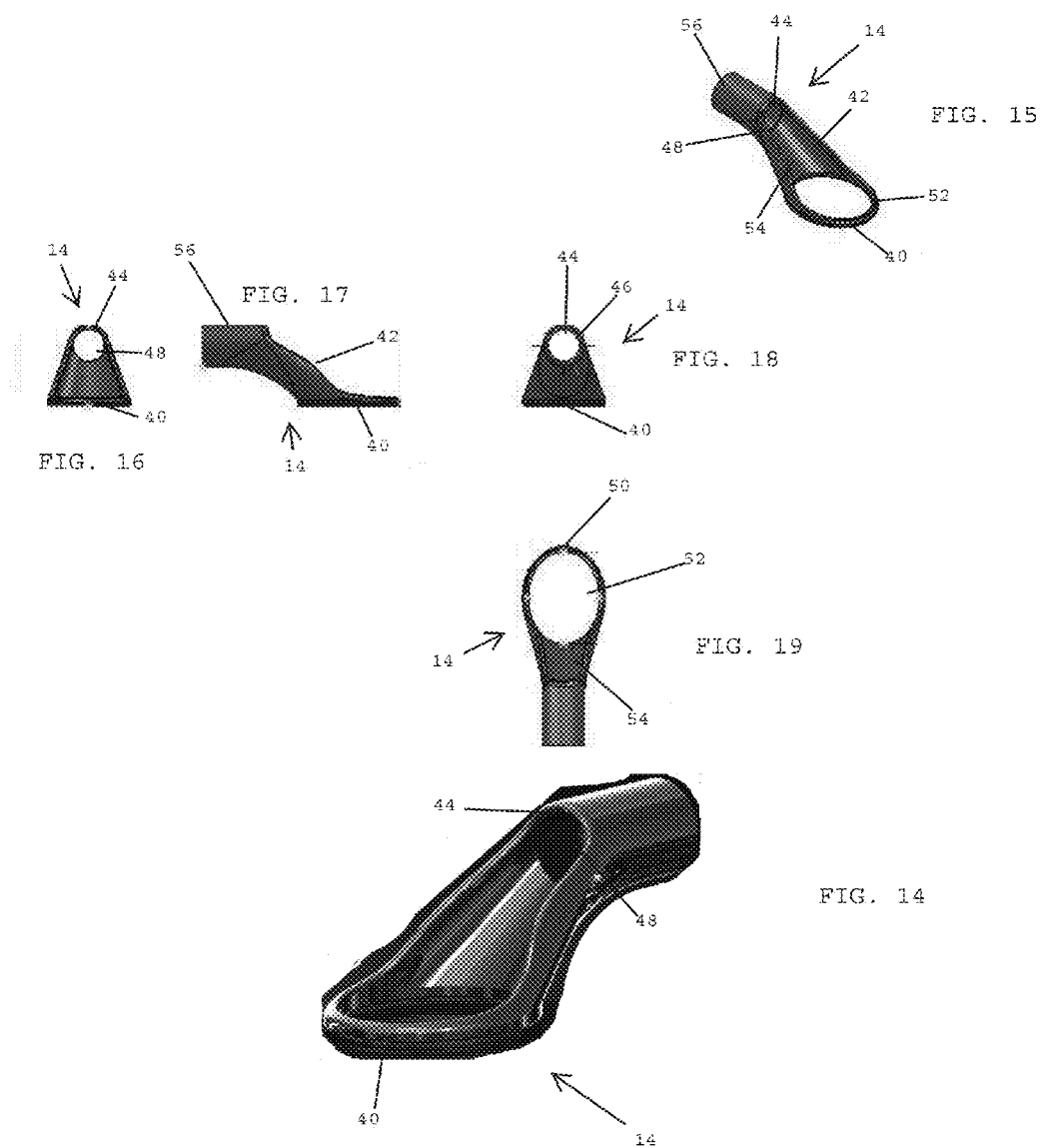

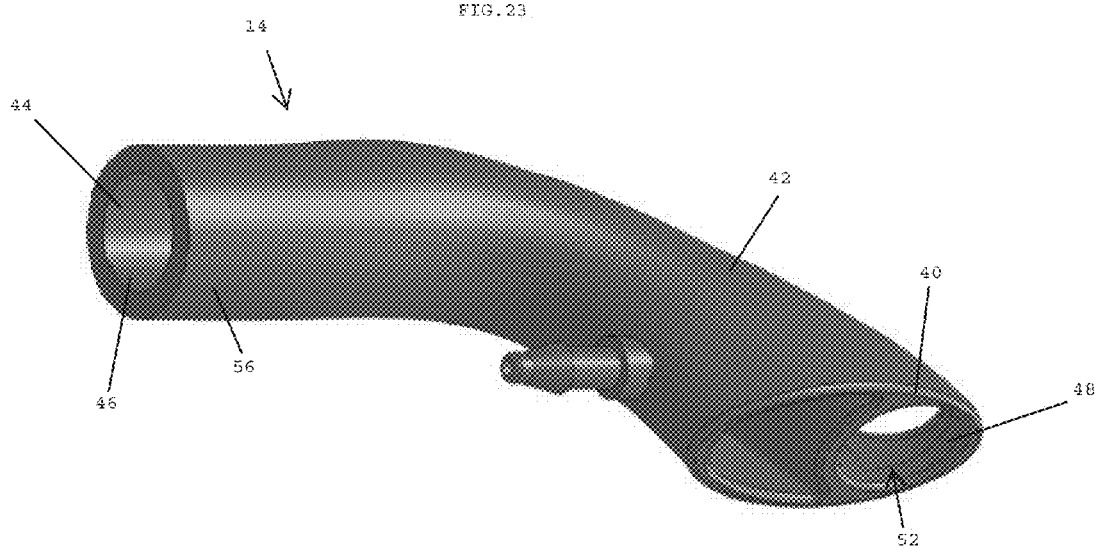

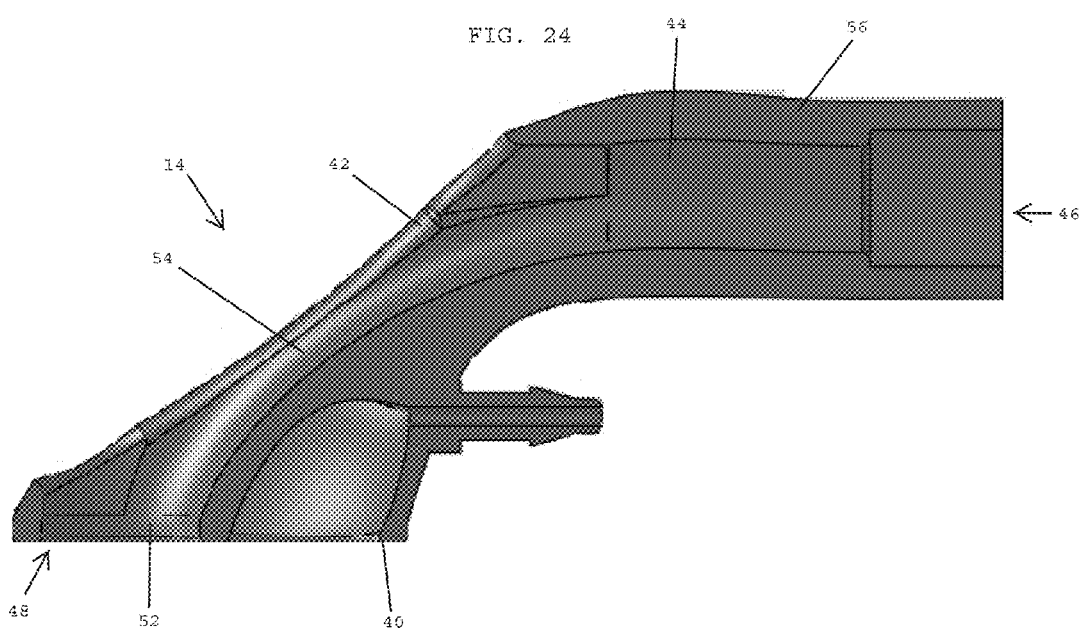

ACCESS DEVICE FOR SURGERY

This application claims priority to and hereby incorporates by reference in its entirety U.S. provisional patent application Ser. No. 61/422,931 filed on Dec. 14, 2010 and entitled "Device for Percutaneous Subxiphoid Access to the Beating Heart Under Direct Visualization."

FIELD OF THE INVENTION

This invention relates to surgical devices and, in particular, devices for providing surgical access within the body of a patient.

BACKGROUND OF THE INVENTION

Although many breakthroughs have been made in cardiovascular medicine, heart disease remains a leading health issue. Despite successful approaches to prevent or retard cardiovascular diseases, it is still very difficult to restore heart function once lost. The recent advances in stem cell research have shown that cells in vital organs, including the heart, can be regenerated. Currently, there are two primary ways of accessing the heart: through a sternotomy or via subxiphoid approach.

A sternotomy, the more traditional approach is used with patients requiring surgery in addition to stem cell therapy. For patients only requiring stem cell therapy, the sub-xiphoid approach is used but tends to be inefficient due to limited visibility and the small workspace. An improved, minimally invasive device, which can safely inject stem cells on the surface of a beating heart, is desirable.

SUMMARY OF THE INVENTION

The present invention overcomes the problems of the prior art by providing an access device for facilitating access, visualization and surgical procedures on tissue structures in a sterile environment.

A method for surgical access includes creating a small-diameter opening in a subject, wherein the opening has a component extending toward an internal structure of the subject. The method also includes advancing a guide member with a guide lumen, wherein the guide lumen includes a curve, through the opening in the subject toward the internal structure. A sterile scope is advanced through the curve of the guide lumen toward the internal structure. And, a surgical procedure is performed on the internal structure of the subject guided by visibility provided by the scope. The method also includes removing the scope from the guide lumen of the guide member.

Another method of surgical access includes creating a small-diameter opening in a subject. The opening has a component extending toward a surface of an internal structure of the subject. A guide member is advanced with a guide lumen through the opening toward the surface of the internal structure. The method also includes advancing a sterile scope through the guide lumen toward the front surface. And, it includes extending the scope out of the guide lumen and around a curved surface of the internal structure of the subject. A surgical procedure is performed on the internal structure of the subject guided by visibility provided by the scope. The method also includes removing the scope from the guide lumen of the guide member.

In another aspect, the surface is a side surface or an inferior surface of the internal structure.

Another method includes administering a therapeutic agent to a subject including sterilely positioning an endoscope, or a sterile portion of the endoscope, into a sterile body space of the subject. A target site is visually identified, using the endoscope, in the sterile body space. Also included is administering the therapeutic agent to the identified target site.

The therapeutic agent may include a pharmaceutical agent, a pacing lead, a graft or a stem cell. The sterile body space may include the pericardial cavity and the target site is cardiac tissue.

A device may also be positioned to elevate the subject's pericardial tissue from the cardiac tissue within the pericardial cavity to create visualization of the cardiac tissue within the cavity prior to administering the therapeutic agent.

The target site may be located beneath pericardial tissue elevated using the device configured to elevate the subject's pericardial tissue.

Another method includes positioning an endoscope, or a portion of an endoscope, in the subject's pericardial cavity. A target site is visually identified on the subject's heart for administration of a therapeutic agent using the endoscope. The method also includes administering the therapeutic agent to the identified target site.

The therapeutic agent may include a pharmaceutical agent, a pacing lead, a graft, a stem cell, biologics or gene therapy. The endoscope, or portion of the endoscope, positioned in the pericardial cavity is sterile. Also, the endoscope may be introduced percutaneaously into the subject.

The method may also include positioning a device configured to elevate the subject's pericardial tissue from its cardiac tissue into the pericardial activity prior to administering the therapeutic agent. The target site may be located beneath the pericardial tissue elevated using the device.

A surgical access device for guiding a scope through a small opening to access a structure inside a subject and positioned next to adjacent tissues may include a guide member and a head member. The guide member has a proximal end and a distal end, wherein the guide member is configured to extend through the small opening. The head member is positioned on the distal end of the guide member and includes a base surface and a tissue elevating surface. The base surface is configured to rest upon the structure inside the subject and the tissue elevating surface is configured to elevate tissues adjacent the structure.

A pathway with a proximal end and a distal end is defined by one, or both, of the guide member and head member. The pathway is configured to receive the scope at the proximal end and guide advancement of the scope through the distal end toward the structure inside the subject to visualize the structure.

In one aspect, the tissue elevating surface extends at an angle to the base surface. The head member and guide member have an average diameter of 20 mm or less from the distal end of the head member to a point between the proximal and distal ends of the guide member.

The pathway may be a channel with an average diameter of 6 mm or less. Also, the channel has a length configured to allow the scope to extend at most 1.5 cm out of the distal end of the channel. For example, the guide member may have a length of at least 15+/−0.5 cm. Also, the channel may include a curved shape between its proximal and distal ends.

In another aspect, the axis of the distal end of the pathway has an angle with respect to a proximal end of the pathway. The angle may be, for example, within a range of 70 degrees to 110 degrees, such as 90 degrees.

The guide member may include a cylindrical shape with a lumen defining a pathway. Also, the guide member may define one or more openings extending from the proximal to distal ends of the guide member.

In another aspect, the small opening is in the sub-xiphoid region or subcostal region of the abdomen and the structure is a heart. The guide member is configured to extend through the sub-xiphoid opening and position the guide member adjacent the surface of the heart. For example, the small opening may be an intercostals opening.

The guide member may be shaped to enable the head member to be extended along a side, top and bottom surfaces of the heart. And, the head member may have a space shape with a pointed or rounded tip defined at its distal end. Defined in the head member may be an opening extending from the tissue elevating surface to the base surface. The peripheral edge of the spade shape extends around the opening and the opening is positioned subjacent the distal end of the pathway.

The opening may have a circular shape and the head member may define a trough extending from the distal end of the pathway to a proximal edge of the opening.

In another aspect, the tissue elevating surface and the base surface are spaced at most 2 cm apart. And, the tissue elevating surface and base surface may form a wedge shape with a thin distal end.

As another option, the head member may be configured to rotate around an axis of the pathway and is controlled by the operator from the handle.

The head member may have a range of volumes adapted for different levels of stabilization of the tissue structure and/or ease of accessibility. For example, the head member may have a volume of 11,029 mm$^3$, 8,865 mm$^3$, or 2,381 mm$^3$ or less. In another embodiment, the head member may define a guide wire opening.

In another aspect, the small opening may be at most 2 cm.

The device may also include a handle mounted to a proximal end of the guide member, wherein the handle partially defines the pathway. The handle may be 40 mm in diameter and is configured to mate with a scope handle. Controls on the handle may couple with controls of the scope.

The pathway may be further configured to guide a scope with a working channel. The scope may be a flexible scope that is 5.3 mm in diameter that is able to withstand conditions of autoclave sterilization and the channel configured to receive such a scope.

The head member and guide member may be comprised of stainless steel that is metal injection molded. The guide member may also include a video camera module coupled to its distal end.

In another aspect, the guide member may be capable of delivering a pacing lead to the heart and inserting or screwing it into the epicardial surface of the heart. The distal guide member may also have an illuminator, such as an illuminating fiber.

These and other features and advantages of the present invention will become more readily apparent to those skilled in the art upon consideration of the following detailed description and accompanying drawings, which describe both the preferred and alternative embodiments of the present invention.

BRIEF DESCRIPTION OF THE DRAWINGS

FIG. 1 is a perspective view of an access device of one embodiment of the present invention;

FIG. 2 is an elevation view of the access device of FIG. 1;

FIG. 3 is a plan view of the access device of FIG. 1;

FIG. 4 is a perspective view of a head member of another embodiment of the present invention;

FIG. 5 is a rear elevation view of the head member of FIG. 4;

FIG. 6 is a plan view of the head member of FIG. 4;

FIG. 10 is a perspective view of a head member of another embodiment of the present invention;

FIG. 11 is an elevation view of the head member of FIG. 10;

FIG. 12 is a plan view of the head member of FIG. 10;

FIG. 13 is a front elevation view of the head member of FIG. 10;

FIGS. 14 and 15 are perspective views of a head member of another embodiment of the present invention;

FIG. 16 is a front elevation view of the head member of FIG. 14;

FIG. 17 is a side elevation view of the head member of FIG. 14;

FIG. 18 is a rear elevation view of the head member of FIG. 14;

FIG. 19 is a plan view of the head member of FIG. 14;

FIG. 23 is a perspective view of a head member of another embodiment of the present invention; and FIG. 24 is a cross-sectional view of the head member of FIG. 23.

DETAILED DESCRIPTION OF THE INVENTION

Figure 9:
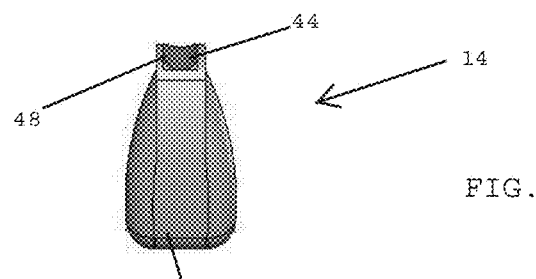
FIG. 9 is a plan view of the head member of FIG. 7.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

Referring to FIGS. 1-3, an embodiment of the present invention includes an access device 10 for facilitating visualization and surgical access through a small opening. The access device includes a guide member 12, a head member 14, and (optionally) a handle 16 which cooperate to define a pathway through the small opening to a tissue structure or structures in the patient's body. For example, the access device 10 may be used to provide access for an endoscope 18 through a subxiphoid incision and under the pericardium to a surface of the heart.

As shown in FIGS. 1-3, the guide member 12 includes a proximal end 20 and a distal end 22. The proximal end 20 is configured to be manipulated from a position distal and external to the patient's body (i.e., more "proximal" to the user). The distal end 22 is sized and configured to insert through a relatively small opening in the patient's body, such as a 2 cm sub-xiphoid incision.

It should be noted that although described in one embodiment as providing access to the heart through a subxiphoid incision, the access device may provide access to a range of tissue structures through varying pathways. For example, access could be provided to other organs, such as the liver, muscles, skeletal structures, etc. Embodiments of the access device 10, however, are best-suited for providing various combinations of visualization and access through small openings (e.g., 2 cm or less through the skin and pericardium) during surgical procedures on curved structures, or through curved pathways, in sterile fields. For example, ranges of diagnostic, therapeutic (including biologics) and observational applications are possible, such as TMR, ablation, echo-probe diagnostics, clip application or isolation of LAA, observation of the same procedures, etc.

The guide member 12 in one embodiment, as shown in FIGS. 1-3, is formed of a tube with a circular cross-section extending from the proximal end 20 to the distal end 22. The circular cross-section defines a tubular shaped lumen or pathway that facilitates passage and directional guiding of the endoscope 18 therethrough. Preferably, the outer diameter of the guide member is at most 20 mm and the inside diameter of the lumen is 6 mm, or another dimension adapted to fit the outside diameter of the endoscope 18.

Other cross-sectional shapes are also possible including square or triangular, or elliptical, depending upon such factors as desired clearance for passage of the endoscope 18 or passage of other instrumentation, some of which will be described hereinbelow. Generally, however, circular cross-sections, or cylindrical (defined broadly to include all extruded shapes, such as an ellipse) cross-sections, are simple and easy to manufacture from existing tube stock using tools such as a pipe bender without generating the strain or pinching of the guide member that might occur with more irregular shapes.

Also, it should be noted that the guide member 12 need not have a closed cross-section and instead could be a channel with an open or u-shaped cross-section or the lumen may have variations in its shape as it extends from the proximal end 20 to the distal end 22. Also, the guide member 12 could include a plurality of lumens, some open, some closed, for separate passage of scopes, fibers, injection needs, fluids, etc.

Preferably, the guide member 12 (and remaining components of the access device 10) is comprised of materials that are able to withstand the temperature, moisture and pressure of an autoclave or other intense sterilization process needed for fields like the thoracic cavity. Also, the guide member (and remainder of the device 10 that's inserted into the patient) is comprised of biocompatible materials that do not create extensive friction with the surrounding tissues. For example, the guide member may be formed of stainless steel or aluminum tube stock having an internal diameter of 6 to 7 mm+/−1 mm sized for passage of at least the endoscope 18 and other desired instrumentation through the tubular passage.

Preferably, the wall thickness and composition of the guide member 12 provide rigidity to withstand the torques of insertion as well as the force of the heart beating. Also, as embodiments of the device 10 should be able to get around the back side of the heart, between the spine and the heart, to deliver injections, and it should be strong enough to lift the entire weight of the heart (approximately 400 g) multiple times throughout its functional lifetime. Sufficient rigidity is also desired to provide feedback to the physician when the head member 14 pushes through the skin or other tissue structures. For example, it could provide feedback on the resistance encountered when spreading the pericardium away from the heart.

The proximal end 20 of the tube has an axis that extends at an angle to the distal end 22 so as to facilitate extension through the sub-xiphoid opening, under the sternum or ribcage, or subcostal region of the abdomen, and toward the heart. The angle in the illustrated embodiment is about 90 to 100 degrees, although the angle may vary for heart access through a range of 70 to 110 degrees depending upon the type of patient (human or animal) and desired approach of the physician. Notably, also, the angle may be further varied for accessing different tissue structures or for different approaches. An intercostal approach through the ribs nearer to the heart may have a much larger angle, with the guide member 12 being nearly straight or only gently curved.

As shown in FIG. 2, the angle between the axes of the proximal end 20 and the distal end 22 is achieved through a continuous arc that itself represents 90 degrees of a circle having a radius of 4-5 inches or 6 inches so as to have a relatively gentle curvature from the proximal to distal ends. This facilitates easy passage of the endoscope with less deflection than a more abrupt angular bend. Notably, such angular pathways are not possible with prior art sterile scopes which have rigid shafts and if they've any ability to maneuver, it is limited to a small portion of the most distal end through a small angle.

The overall length of the guide member 12 is sufficient to extend through the sub-xiphoid incision and reach the heart in the majority of human patients. For example, the length may be at least 15+/−0.5 cm. Preferably, the length and angle of the guide member 12 are sufficient, in combination, to provide access to side, top and bottom surfaces of the heart. The preferred tolerance of the lumen in the guide member 12, and for other tolerances affecting the placement of the end of the endoscope 18, is +/−0.1 mm or even +/−0.025 mm.

As shown in FIGS. 1-3 and 20-21, the handle 16 is fixed to the proximal end 20 of the guide member 12 and the guide member may extend into the handle 30. The handle 30 has a generally elongate shape with a plurality of grip ridges 24 positioned to facilitate firm gripping about an axis of the elongate shape. The handle has a diameter of approximately 40 mm to provide a good ergonomic balance between contact area and gripping force for operation by a single surgeon or healthcare worker. This diameter, however, could be varied for a custom fit to different healthcare personnel. Also, an additional healthcare worker may be needed for deployment of devices down the working channel of the endoscope 18.

A handle opening 26 with a cylindrical cross-section configured to receive the outer diameter of the guide member 12 is defined along the axis of the handle 16. The guide member 12 may be secured therein with an adhesive, welding, fastener or other securement to reduce relative movement between the two. The handle opening 26 may have two diameters, the smaller diameter at a distal end 28 configured to receive the guide member 12 and a wider diameter at its proximal end 30. The proximal end 30 has a diameter configured to firmly receive a distal end of a handle 32 of the endoscope 18. In one embodiment, as shown in FIG. 3, the smaller diameter at distal end 28 is 9.6 mm and the diameter at the proximal end 30 is 23.9 mm.

Figure 20:
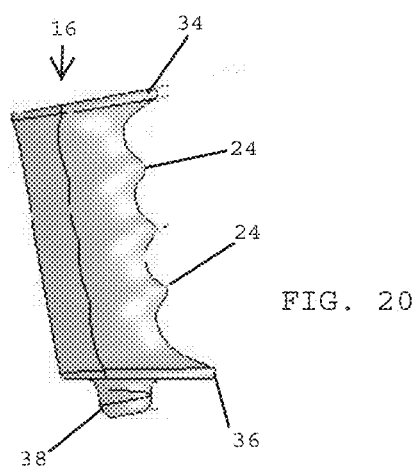
FIGS. 20 and 21 are perspective views of a handle of the access device of FIG. 1.
Figure 21:
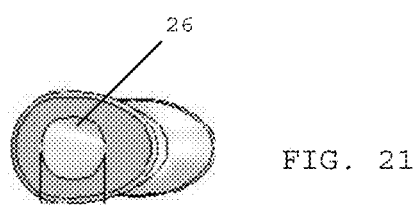
Figure 22:
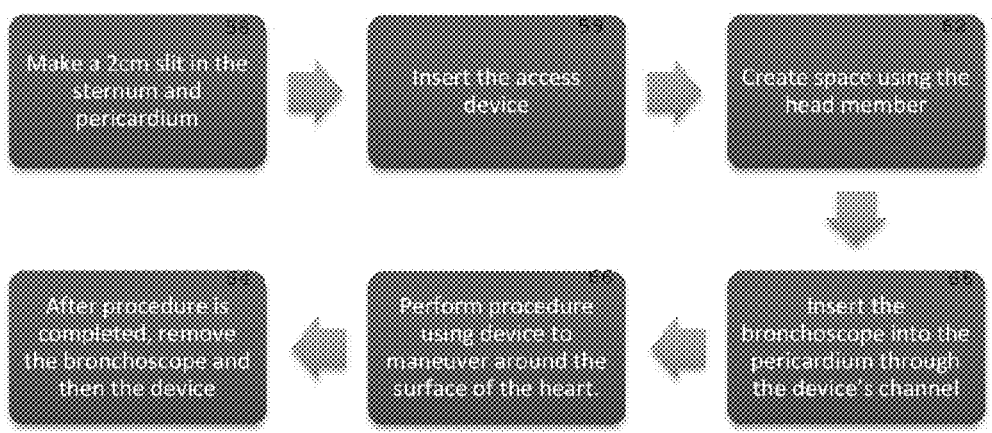
FIG. 22 is a method of using an access device of another embodiment of the present invention.

The handle 16 may also include top and bottom flanges 34, 36 with elliptical shapes that extend out further than the grip ridges 24 and help to avoid slippage of the handle in the user's grip. Also, the handle 16, as shown in FIGS. 20-21, may include a stability extension 38 that extends along an additional length of the guide member 12 for additional stability.

Other dimensions of the handle 16 in one embodiment include a total length of 121 mm, a distance between the flanges of 105.5 mm, between the grip ridges of 23.9 mm, a length of the flanges of 59.5 mm, a width of 42.7 mm for top flange 34 or 37.6 mm for bottom flange 36. The stability extension may have an outer diameter of 20 mm and a radius as it tapers from the bottom flange 36 of 5 mm.

As shown in FIGS. 1-3, the head member 14 of one embodiment includes a base surface 40 and a tissue elevating surface 42 and defines a head opening 44. Generally, the base surface 40 is configured to rest upon a base tissue structure, such as the heart, and the elevating surface 42 is configured to elevate (herein broadly defined as separating, not just moving against gravity) adjacent tissue, such as the pericardium, away from the base tissue structure. The base surface 40 may include a plurality of teeth to facilitate gripping of the surface of the heart or other tissues.

The head opening 44 has a proximal end 46 configured to fit over the distal end 22 of guide member 12 and to be attached firmly thereto, or the head member 14 and guide member 12 may be formed from the same material. Regardless, a distal end 48 of the head opening 44 is configured to cooperate with the opening in the guide member 12 and the handle opening 26 to form a continuous pathway for guiding the endoscope 18 through the opening in the patient and to the relevant tissue structure.

In one embodiment, as shown in FIGS. 14-19, the head member 14 has the shape of a spade and includes the additional features of a proximal mounting portion 56, a pointed or rounded tip 50, a view opening 52 and a trough 54. The proximal mounting portion 56 has a cylindrical shape and defines the proximal end 46 of the head opening and is configured to fit over the distal end 22 of guide member 12 to secure the head member 14 thereto. Preferably, the outer diameter of the proximal mounting portion 56 is similar to the distal end of the guide member 12 so as to facilitate a smooth transition therebetween.

The spade shape of the head member, as shown in a plan view in FIG. 19, is defined by a peripheral edge that extends away from the proximal mounting portion 56, flaring outward and then tapering inward until it reaches the pointed or rounded tip 50. Preferably, this spade shape is configured to facilitate pressing the head member 14 through adjacent tissues to separate them for visibility purposes.

The trough 54 extends down from the distal end 44 of head opening toward view opening 52 with a smooth arc shape and a slight flare as it feeds into the view opening, as shown in FIG. 14. Lateral edges bracket the trough 54 and also extend toward the view opening 52. Together, the shape of the trough and the lateral edges help to guide the distal end of the endoscope 18 toward the view opening 52.

The view opening 52 has a circular or elliptical shape and is bounded by the peripheral edge of the head member 14. The proximal edge of the view opening intersects the end of the trough 54.

The base surface 40 includes the relatively flat undersurface of the head member that is configured to rest upon the surface of adjacent tissue, such as the heart. For example, the underside of the peripheral edge extending around the view opening 52 may be the base surface 40. The tissue elevating surface 42 includes the top surface of the same peripheral edge and the top of the lateral edges of the trough 54. Extending between these two surfaces is the view opening 52.

Generally, the tissue elevating surface 42 extends at a diverging angle from the base surface 40 as it extends proximally from the pointed or rounded tip 50 so as to form a wedge shape to help pry apart or separate adjacent tissues and provide access for the endoscope and a viewing field. In further detail, the tissue elevating surface extends relatively flat and in parallel with the base surface 40 from the pointed or rounded tip 50 and then convexly curves upward from there in the proximal direction to the portion of the head member defining the distal end 48 of head opening 44. The tissue elevating surface also includes the dorsal or top surface of the proximal portion defining the head opening. The base surface may similarly include an arcing portion that extends concavely upward from its flat distal portion.

The volume of the head member 14 can have an impact on its performance, depending upon the application, and for the application of providing access and visibility to the heart under the pericardium is 11,029 mm$^3$ or less. Easier access is facilitated with even smaller volumes, for example the head member volume can be 8,865 mm$^3$ or less, or of 2,381 mm$^3$ or less, or of 1,275 mm$^3$ or less, with the smaller range being better suited to the embodiment described hereinabove.

Other dimensions of the head member 14 embodiment illustrated in FIGS. 14-19 include 10 mm outside diameter and 7.5 mm inside diameter. The view opening 52 has a primary diameter of 22 mm and a small, lateral diameter of 17 mm. The overall height of the head member 14 is preferably less than 20 mm for elevation of the pericardium, such as 19.5 mm for lifting the pericardium from the heart. Notably, although these ranges are particularly advantageous, it is still possible to mix and/or combine with other ranges stated herein and still be within the scope of the present invention.

Advantages of the embodiment of FIGS. 14-19 include a stable base and, due to the thinness of the metal ellipse, enabling the surgeon to look out over the surface of the heart for accurate navigation. The somewhat larger cross sectional area, however, would require a slightly larger slit in the skin and pericardium for insertion.

In another embodiment, as shown in FIGS. 10-13, the head member has a more compact elliptical rim with a somewhat thicker construction. For example, dimensions of the head member 14 include a 10.714 mm outside diameter, 7.5 mm inside diameter and 31.429 mm length of the proximal end. The view opening 52 has a primary radius of 8.370 mm and a small lateral radius of 5.905 mm. The overall height of the head member 14 is 18.750 mm and its volume is 2,381 mm$^3$. An advantage of this embodiment is that it requires a smaller opening to reach the heart or other tissue structure. However, because of its smaller size, the provided visibility is not as good as the prior embodiment, nor is the stability of the base surface.

Figure 8:
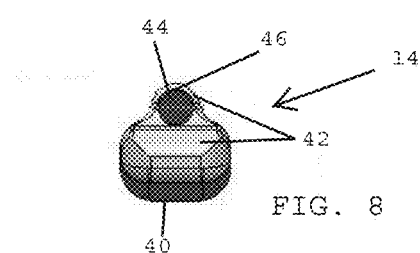
FIG. 8 is a rear elevation view of the head member of FIG. 7.
Figure 7:
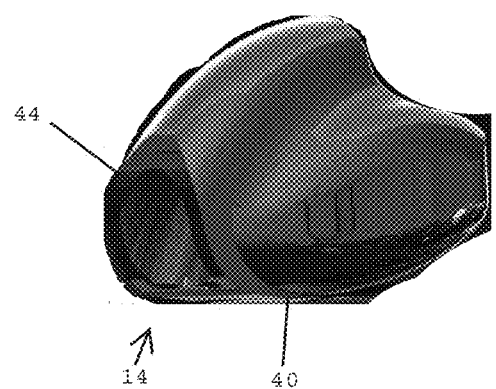
FIG. 7 is a perspective view of a head member of another embodiment of the present invention.

In yet another embodiment, as shown in FIGS. 7-9, the head member 14 has a more gradual slope for lifting the pericardium and a smooth "torpedo" shape for lifting the pericardium about 25 mm from the heart. This provides a relatively good field of view and less vertical distance is needed for an injection, but the injection angle is limited somewhat to 45-60 degrees. The embodiment is rather bulky however at a volume of 11,029 mm$^3$. Other dimensions include a 7.5 mm diameter passage that extends from the proximal-dorsal position to the distal tip of the head member 14. The head member has a proximal width of 23.484 mm and narrows to a distal width of 10.476 mm. Its maximum height is 25.445 mm at the proximal end and extends to a rounded distal end of 9.127 mm radius. The length of the portion defining the passageway is 31.187 mm and the overall length is 43.814 mm.

Another embodiment of the head member 14 is shown in FIGS. 4-6 and has a relatively wide base, somewhat similar to the prior embodiment, for endoscope stability and a wedge shape to promote sliding of the pericardium. The injection angle permitted is larger from 45 to 90 degrees. Its lift height is 26.250 mm for the pericardium which is less desired due to the pressure exerted on the heart. Generally, a pressure of less than 15 psi is desired to avoid rupture. Also, the wedge-shaped front limits visibility compared to the hoop embodiments. Further, like the prior embodiment, it is a relatively bulky embodiment with a volume of 8,865 mm³. Notably, however, these alternative embodiments may be more effective with different tissue structures or access pathways. Other dimensions include 7.5 mm diameter passageway, a top attachment portion with a 10.5 mm diameter, a base portion with a 23.479 mm width, a length of 40.6 mm and 6 mm radii for a transition between the top and base portions and on the lateral sides of the base portion.

In yet another embodiment, the head member 14 may be axially rotatable 180 degrees to access surfaces in the other direction, such as a bottom surface of the heart ventricle. Also, the head member 14 may be capable of multiple axis of rotation and/or displacements, such as controlled flexion/extension within the plane of the guide member 12 or lateral (side-to-side) divergences of the head member 14. These rotations may be controlled by wires extending down through or along lumens in the guide member 12 to the head member 14 which is mounted flexibly or pivotally on the distal end 22 of the guide member.

The endoscope 18 is preferably a steam autoclavable flexible scope such as the Olympus BF Q180-CA. When combined with the access device 10, this enables procedures to be performed in a normally sterile environments or fields (such as the thoracic cavity) requiring visibility and for which chemical sterilization is inadequate. Specifications of the preferred endoscope 18 include a 5.3 mm outer diameter, 2 mm working channel, 600 mm working length, a 180°/130° angle of curvature and a 120° field of view. Preferably, the length of the guide opening of the access device is configured to allow only about 1.5 cm of the tip of the endoscope 18 to extend out of the head member 14.

The working channel of the endoscope 18 is configured to receive and pass therethrough a flexible needle attached to a syringe containing stem cells. The distal end of the need extends out of the working channel and the adjustability of the endoscope 18 tip advantageously allows the injection to be precisely controlled (2 mm of precision) to be perpendicular to the heart.

In another aspect, the endoscope 18 is configured to use narrow band imaging with discrete bands of blue and green light that highlights the blood vessels, thereby facilitating accurate injection into the heart. A photosensitive dye could be used to increase the contrast of the vasculature by fluorescing under certain lights, such as UV or IR or near-IR, so that these vessels may be avoided or, where applicable targeted, with various treatments.

In another embodiment, the head member 14 may be inflatable.

The access device 10 and it various components are preferably able to withstand the heat, pressure and moisture of a steam autoclave. Metal injection molding (MIM) may be used to manufacture the access device 10 or its components out of stainless steel and affords the low cost of injection molding with the accuracy of machining Cost constraints for MIM appear to drop off after 10,000 or more units are manufactured. MIM also offers good tolerances of 0.025 mm, within the desired tolerance of 0.1 mm.

Packaging for the access device 10 may include storage in a clean pouch with sterilization at the healthcare facility using standard steam autoclaving. The access device 10 is then kept between 18 and 25° C. with at least two air changes per hour at a relative humidity of 25% to 50%. Also, the access device 10 can be kept on hard, closed shelving at least 30 cm from the floor, 5 cm from outside walls and 50 cm from the ceiling to preserve its sterile condition.

The access device 10 may be used in a range of applications, such as clamping of the left-atrial-appendage (LAA), treatment of atrial fibrillation by ablation of the surface of the heart (such as the left ventricle), bypass graft surgery and pacemaker repair or placement, such as placement of the leads. LAA clamping may be facilitated by approaching the LAA from two different directions, such as from a transseptal approach and the sub-xiphoid approach at the same time. For example, a balloon is used to fill the LAA internally and the access device 10 is employed to deploy a lasso or other isolating device to the external surface of the LAA. Also, the endoscope 18 may provide visualization of such a procedure.

Lead placement or ablation may involve the use of an electrical sensor for application to the heart via the access device 10. And, the lead may be a screw-in pacing lead that's mounted to the head member 12 under illumination from the endoscope 18's light and visualization capacities. In another example, an electrophysiology (EP) test is conducted through vasculature, such as through the femoral artery, while the ablation to correspond with detection of arrhythmia is performed using the access device 10. EP could also be used to locate ventricular tachycardia foci on the left ventricle to facilitate ablation.

In addition to stem cells, other therapeutics, glues or fasteners could be applied to the heart. Also, the access device 10 could provide post operative care or inspection. For example, it could be used assess vein or arterial bypass grafting for bleeding, or other sites for post-op bleeding.

In yet another embodiment, various components of the access device 10 and/or the endoscope 18 may be integrated for a more compact, affordable or effective device. For example, light and camera function may be integrated into the head member or some distal portion of the access device 10. For example, the head member 12 may include a CCD or other imaging chip (an electronic micro-camera) to negate the need for the scope tube, allowing it to communicate data instead of an analog optical image. Such a camera may also be employed in conjunction with the endoscope 18. A fiber could be run through the guide member 12 to provide illumination. Similarly, controls on the handle 16 could replace or mate with the controls of the endoscope 18.

In another embodiment, the guide member 12 may include additional guides or lumens or side board mechanisms configured for delivery of additional tools outside of the endoscope 18's working channel, such as down one side of the guide member. These additional lumens may be employed, for example, in deployment of echo-probes, or other ultrasound instruments, or for diagnostics or lasers for transmyocardial revascularization (TMR). The working channel of the endoscope 18, if sufficiently large, may also afford deployment of these lasers, probes or other instruments.

In another embodiment, the head member 14 may be modified for a "monorail" application wherein an opening extends through the head member to allow it to be applied over a guide wire that's first inserted through the sub-xiphoid approach and into the pericardium (or some other selected minimally-invasive approach).

Another embodiment of the head member 14 is shown in FIGS. 23 and 24. The height of the head member from the base surface 40 to the top of the proximal mounting portion 56 is 1.15 inches. The angle from the base surface to the beginning of the proximal mounting portion is about 36 degrees, or 36.3 degrees. The view opening 52 is somewhat smaller at 0.4 inch×0.32 inch to allow clearance for a suction passageway 70 that extends in a moon shape around the edge of the base surface 40 defining the view opening 52. The suction passageway 70 extends along the head member 14 and is connected in communication with a suction nipple 72. The suction nipple extends away from the head member to provide a mount for a suction line. Use of suction advantageously secures the head member 14 even further to the underlying tissue, such as a beating heart which tends to move during beating-heart procedures. Thus the suction helps to stabilize the tissue. The long axis of the base surface 40 is about 1 inch by about 0.5 inch on the small axis, leaving about 0.6 inch for the trough-to-crest length of the suction passageway 70.

A method of providing access includes making 58 a 2 cm slit in the sternum and pericardium. The access device 10 is inserted 60 through the slit. Space is created 62 using the head member 14. The bronchoscope is inserted 64 through the access device 10 into the pericardium using the channel defined by the access device 10. A procedure is performed 66 using the access device 10 to maneuver around the surface of the heart. After completion of the procedure, the bronchoscope is removed 68 and the access device is removed.

A number of aspects of the systems, devices and methods have been described. Nevertheless, it will be understood that various modifications may be made without departing from the spirit and scope of the disclosure. Accordingly, other aspects are within the scope of the following claims.

That which is claimed:

1. A surgical access device for guiding a scope through a small opening to access a structure inside a subject and positioned next to adjacent tissues, the access device comprising:
   a guide member having a proximal end and a distal end, the guide member configured to position the guide member adjacent the surface of a heart; and
   a head member positioned on the distal end of the guide member, the head member including a base surface, a tissue elevating surface proximal to the base surface, and a head opening proximal to the tissue elevating surface;
   wherein the base surface comprises a peripheral edge that defines a view opening having an elliptical shape and is configured to rest upon the heart inside the subject;
   wherein the tissue elevating surface extends proximally from the base surface toward the head opening at an angle suitable to elevate pericardial tissues adjacent the heart;
   wherein the head opening has a proximal end and a distal end, the proximal end of the head opening being configured to cooperate with the distal end of the guide member to define a continuous pathway with a proximal end and a distal end, the pathway configured to receive the scope at the proximal end and guide advancement of the scope through the distal end toward the heart inside the subject to visualize the heart; and
   wherein the head opening is configured to provide the scope with an unconstrained view of the surface of the heart for navigation while the base surface is in contact with the surface of the heart.

2. The surgical access device of claim 1, wherein the pathway is a channel.

3. The surgical access device of claim 1, wherein the head member has a spade shape.

4. The surgical access device of claim 3, wherein a rounded tip of the spade shape defines a distal end of the head member.

5. The surgical access device of claim 1, wherein the tissue elevating surface and the base surface are spaced at most 2 cm apart.

6. The surgical access device of claim 5, wherein the tissue elevating and base surfaces form a wedge shape with a thin distal end.

7. The surgical access device of claim 1, wherein the head member is configured to rotate around an axis of the pathway controlled by the operator from the handle.

8. The surgical access device of claim 1, wherein the head member defines a guide wire opening.

9. The surgical access device of claim 1, further comprising a handle mounted to the proximal end of the guide member.

10. The surgical access device of claim 9, wherein the handle partially defines the pathway.

11. The surgical access device of claim 10, wherein the handle is configured to connect to a handle of the scope.

12. The surgical access device of claim 1, wherein the pathway is configured to receive and guide a scope with a working channel.

13. The surgical access device of claim 1, wherein the head member and guide member comprise stainless steel.

14. The surgical access device of claim 1, wherein the guide member is configured to extend through a small sub-xiphoid or subcostal opening and position the guide member adjacent the surface of the heart.

15. The surgical access device of claim 1, wherein an axis of the distal end of the pathway has an angle in a range of 70 degrees to 110 degrees with respect to an axis of the proximal end of the pathway.

* * * * *